US006455501B1

(12) United States Patent
Rodgers et al.

(10) Patent No.: US 6,455,501 B1
(45) Date of Patent: *Sep. 24, 2002

(54) WOUND HEALING COMPOSITIONS

(75) Inventors: Kathleen E. Rodgers, Long Beach, CA (US); Gere S. DiZerega, Pasadena, CA (US)

(73) Assignee: University of Southern California, Los Angeles, CA (US)

( * ) Notice: Subject to any disclaimer, the term of this patent is extended or adjusted under 35 U.S.C. 154(b) by 71 days.

This patent is subject to a terminal disclaimer.

(21) Appl. No.: 09/698,354

(22) Filed: Oct. 27, 2000

Related U.S. Application Data

(63) Continuation of application No. 09/210,249, filed on Dec. 11, 1998, now Pat. No. 6,165,978.
(60) Provisional application No. 60/069,662, filed on Dec. 12, 1997.

(51) Int. Cl.$^7$ ............................. A61K 38/08; C07K 7/14
(52) U.S. Cl. ......................... 514/16; 514/17; 530/328; 530/329
(58) Field of Search ...................... 514/16, 17; 530/328, 530/329

(56) References Cited

U.S. PATENT DOCUMENTS

| | | |
|---|---|---|
| 5,015,629 A | 5/1991 | diZerega |
| 6,165,978 A * | 12/2000 | Rodgers et al. |

FOREIGN PATENT DOCUMENTS

| | | |
|---|---|---|
| WO | WO 95/08337 | 3/1995 |
| WO | WO 95/08565 | 3/1995 |
| WO | WO 96/14858 | 5/1996 |
| WO | WO 96/39164 | 12/1996 |
| WO | WO 98/26795 | 6/1998 |
| WO | WO 98/32457 | 7/1998 |
| WO | WO 98/33813 | 8/1998 |

OTHER PUBLICATIONS

Ambuhl et al., (1992) Regulatory Peptides, 38:111–120.
Bell et al., (1990) Am. J. Pathol., 137:7–12.
Bell et al., (1992) J. Clin. Invest., 89:315–320.
Brattstrom et al., (1992) Progress in Brain Research, 91:75–79.
Dzau et al., (1989) J. Mol. Cell Cardiol., 21:S7.
Fermandjian et al., (1981) Biopolymers, 20:1971–1983.
Fernandez et al., (1985) J. Lab. Clin. Med., 105:141–145.
Gibbons et al., (1992) J. Clin. Invest., 90:456–461.
Greenhalgh et al., (1990) Am. J. Pathol., 136:1235–1246.
Hunt et al., (1981) in The Surgical Wound, F. Dineen & G. Hildrick–Smith, eds. (Lea & Febiger, Philadelphia), pp. 1–18.
Jorgensen et al., (1971) J. Med. Chem., 14:899–903.
Kawahara et al., (1988) Biochem. Biophys. Res. Comm. 150:52–59.
Khosla et al., (1980) Peptide Chemistry, 17:123–126.
Kimura et al., (1992) Biochem. Biophys. Res. Comm., 187:1083–1090.
LeNoble et al., (1991) Eur. J. Pharmacol., 195:305–306.
Lintner et al., (1975) FEBS Letters, 56:366–369.
Lynch et al., (1989) J. Clin. Invest., 84:640–646.
Naftilan et al., (1989) J. Clin. Invest., 83:1419–1424.
Nakahara et al., (1992) Biochem. Biophys. Res. Comm., 184:811–818.
Novotny et al., (1969) Bratisl Lek. Listy, 52:298–302.
Osterriedes et al., (1991) Hypertension, 18:Suppl II60–64.
Powell et al., (1991) J. Cardiovasc. Pharmacol. 16(suppl 4):S42–49.
Samanen et al., (1989) J. Med. Chem., 32:466–472.
Taubman et al., (1989) J. Biol. Chem., 264:526–530.
Vatta et al., (1992) Can. J. Physiol. Pharmacol., 70:821–825.
Viswanathan et al., (1992) Peptides, 13:783–786.
Wade et al., (1997) Protein Peptide Letters, 4:87–90.
Wolf et al., (1992) Am. J. Pathol., 140:95–107.

* cited by examiner

Primary Examiner—Christopher S. F. Low
Assistant Examiner—Anish Gupta
(74) Attorney, Agent, or Firm—McDonnell Boehnen Hulbert & Berghoff; David S. Harper

(57) ABSTRACT

Methods and compositions based on chemical analogs of angiotensin II and analogs of angiotensin II fragments useful for accelerating wound healing in mammals.

14 Claims, 13 Drawing Sheets

SEQUENCE LISTING

```
<160> NUMBER OF SEQ ID NOS:  15

<210> SEQ ID NO 1
<211> LENGTH: 8
<212> TYPE: PRT
<213> ORGANISM: Artificial Sequence
<220> FEATURE:
<223> OTHER INFORMATION: Synthetic peptide

<400> SEQUENCE: 1

Asp Arg Val Tyr Ile His Pro Phe
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2

Arg Val Tyr Ile His Pro Phe
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic peptide

<400> SEQUENCE: 3

Tyr Ile His Pro Phe
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic peptide
<221> NAME/KEY: VARIANT
<222> LOCATION: (4)...(4)
<223> OTHER INFORMATION: Xaa(4) is Tyr(PO3)2
```

```
<400> SEQUENCE: 4

Asp Arg Val Xaa Ile His Pro Phe
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic peptide
<221> NAME/KEY: VARIANT
<222> LOCATION: (3)...(3)
<223> OTHER INFORMATION: Xaa(3) is norLeu

<400> SEQUENCE: 5

Asp Arg Xaa Tyr Ile His Pro Phe
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic peptide
<221> NAME/KEY: VARIANT
<222> LOCATION: (5)...(5)
<223> OTHER INFORMATION: Xaa(5) is norLeu

<400> SEQUENCE: 6

Asp Arg Val Tyr Xaa His Pro Phe
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic peptide
<221> NAME/KEY: VARIANT
<222> LOCATION: (4)...(4)
<223> OTHER INFORMATION: Xaa(4) is homoSer

<400> SEQUENCE: 7

Asp Arg Val Xaa Ile His Pro Phe
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic peptide

<400> SEQUENCE: 8

Asp Arg Val Tyr Ile His Pro Ile
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide
<221> NAME/KEY: VARIANT
<222> LOCATION: (2)...(2)
<223> OTHER INFORMATION: Xaa(2) is norLeu

<400> SEQUENCE: 9
```

Arg Xaa Tyr Ile His Pro Phe
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic peptide
<221> NAME/KEY: VARIANT
<222> LOCATION: (4)...(4)
<223> OTHER INFORMATION: Xaa(4) is norLeu

<400> SEQUENCE: 10

Arg Val Tyr Xaa His Pro Phe
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic peptide
<221> NAME/KEY: VARIANT
<222> LOCATION: (3)...(3)
<223> OTHER INFORMATION: Xaa(3) is Val or norLeu
<221> NAME/KEY: VARIANT
<222> LOCATION: (4)...(4)
<223> OTHER INFORMATION: Xaa(4) is Tyr, Tyr(PO3)2 or homoSer
<221> NAME/KEY: VARIANT
<222> LOCATION: (5)...(5)
<223> OTHER INFORMATION: Xaa(5) is Ile or norLeu
<221> NAME/KEY: VARIANT
<222> LOCATION: (8)...(8)
<223> OTHER INFORMATION: Xaa(8) is Phe or Ile

<400> SEQUENCE: 11

Asp Arg Xaa Xaa Xaa His Pro Xaa
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic peptide
<221> NAME/KEY: VARIANT
<222> LOCATION: (2)...(2)
<223> OTHER INFORMATION: Xaa(2) is Val or norLeu
<221> NAME/KEY: VARIANT
<222> LOCATION: (3)...(3)
<223> OTHER INFORMATION: Xaa(3) is Tyr, Tyr(PO3)2 or homoSer
<221> NAME/KEY: VARIANT
<222> LOCATION: (4)...(4)
<223> OTHER INFORMATION: Xaa(4) is Ile or norLeu
<221> NAME/KEY: VARIANT
<222> LOCATION: (7)...(7)
<223> OTHER INFORMATION: Xaa(7) is Phe or Ile

<400> SEQUENCE: 12

Arg Xaa Xaa Xaa His Pro Xaa
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic peptide
<221> NAME/KEY: VARIANT
<222> LOCATION: (3)...(3)
<223> OTHER INFORMATION: Xaa(3) is Val or norLeu

```
<221> NAME/KEY: VARIANT
<222> LOCATION: (4)...(4)
<223> OTHER INFORMATION: Xaa(4) is Tyr, Tyr(PO3)2 or homoSer
<221> NAME/KEY: VARIANT
<222> LOCATION: (5)...(5)
<223> OTHER INFORMATION: Xaa(5) is Ile or norLeu

<400> SEQUENCE: 13

Asp Arg Xaa Xaa Xaa His Pro
 1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic peptide
<221> NAME/KEY: VARIANT
<222> LOCATION: (2)...(2)
<223> OTHER INFORMATION: Xaa(2) is Val or norLeu
<221> NAME/KEY: VARIANT
<222> LOCATION: (3)...(3)
<223> OTHER INFORMATION: Xaa(3) is Tyr, Tyr(PO3)2 or homoSer
<221> NAME/KEY: VARIANT
<222> LOCATION: (4)...(4)
<223> OTHER INFORMATION: Xaa(4) is Ile or norLeu

<400> SEQUENCE: 14

Arg Xaa Xaa Xaa His Pro
 1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic Peptide
<221> NAME/KEY: VARIANT
<222> LOCATION: (3)...(3)
<223> OTHER INFORMATION: Xaa(3) is norLeu

<400> SEQUENCE: 15

Asp Arg Xaa Tyr Ile His Pro
 1               5
```

WOUND HEALING COMPOSITIONS

RELATED APPLICATIONS

This application is a continuation of U.S. patent application Ser. No. 09/210,249 filed Dec. 11, 1998, now U.S. Pat. No. 6,165,978 which claims the benefit of priority under 35 U.S.C. §119(e) of U.S. Provisional Patent Application Ser. No. 60/069,662 filed Dec. 12, 1997, which is incorporated by reference in its entirety.

FIELD OF THE INVENTION

This invention relates generally to the fields of biochemistry and medicine. More particularly, the present invention relates to compositions and methods useful for accelerating wound healing in mammals.

BACKGROUND OF THE INVENTION

Wounds (i.e., lacerations or openings) in mammalian tissue result in tissue disruption and coagulation of the microvasculature at the wound face. Repair of such tissue represents an orderly, controlled cellular response to injury. All soft tissue wounds, regardless of size, heal in a similar manner. Tissue growth and repair are biologic systems wherein cellular proliferation and angiogenesis occur in the presence of an oxygen gradient. The sequential morphological and structural changes which occur during tissue repair have been characterized in great detail and have in some instances been quantified [Hunt, T. K., et al., "Coagulation and macrophage stimulation of angiogenesis and wound healing," in *The surgical wound*, pp. 1–18, ed. F. Dineen & G. Hildrick-Smith (Lea & Febiger, Philadelphia: 1981)].

The cellular morphology consists of three distinct zones. The central avascular wound space is oxygen deficient, acidotic and hypercarbic, and has high lactate levels. Adjacent to the wound space is a gradient zone of local anemia (ischemia) which is populated by dividing fibroblasts. Behind the leading zone is an area of active collagen synthesis characterized by mature fibroblasts and numerous newly-formed capillaries (i.e., neovascularization). While this new blood vessel growth (angiogenesis) is necessary for the healing of wound tissue, angiogenic agents generally are unable to fulfill the long-felt need of providing the additional biosynthetic effects of tissue repair. Despite the need for more rapid healing of wounds (i.e., severe burns, surgical incisions, lacerations and other trauma), to date there has been only limited success in accelerating wound healing with pharmacological agents.

U.S. Pat. No. 5,015,629 to DiZerega (the entire disclosure of which is hereby incorporated by reference) describes a method for increasing the rate of healing of wound tissue, comprising the application to such tissue of angiotensin II (AII) in an amount which is sufficient for said increase. The application of angiotensin II to wound tissue significantly increases the rate of wound healing, leading to a more rapid re-epithelialization and tissue repair. The term angiotensin II refers to an octapeptide present in humans and other species having the sequence Asp-Arg-Val-Tyr-Ile-His-Pro-Phe (SEQ ID NO:1). Angiotensin II is a known pressor agent and is commercially available.

Angiotensin III (AIII) is a biologically active compound derived from AII by removal of a single amino acid from the N-terminus of AII. Thus, AIII has the sequence Arg-Val-Tyr-Ile-His-Pro-Phe (SEQ ID NO:2). In spite of the apparent structural relatedness of AII and AIII, these molecules exhibit a range of finctional differences. For example, AII showed a biphasic effect on evoked neuronal norepinephrine release (an earlier decrease followed by a later increase), while increasing spontaneous norepinephrine release only after 12 minutes; AIII showed a biphasic effect on both evoked and spontaneous neuronal norepinephrine release [Vatta, M. S., et al. (1992), Monophasic and biphasic effects of angiotensin II and III on norepinephrine uptake and release in rat adrenal medulla, *Can. J. Physiol. Pharmacol.* 70:821]. Moreover, AII and AIII show differential influences on the baroreceptor-hear-reflex: AII enhances the sensitivity of the reflex, whereas AIII impairs it [Brattstrom, A., et al. (1992), Neuropeptides within the nucleus tractus solitarii modulate the central cardiovascular control process, *Progress in Brain Research* 91:75].

SUMMARY OF THE INVENTION

A first aspect of the invention relates to a composition that is useful for accelerating wound healing. This composition includes a suitable carrier or diluent and an amount effective to accelerate wound healing of at least one compound having at least five contiguous amino acids of a general formula that can be any one of:

$R^1$-Arg-norLeu-$R^3$-$R^4$-His-Pro-$R^5$ (SEQ ID NO:11),
$R^1$-Arg-$R^2$-Tyr(PO$_3$)$_2$-$R^4$-His-Pro-$R^5$ (SEQ ID NO:12),
$R^1$-Arg-$R^2$-homoSer-$R^4$-His-Pro-$R^5$ (SEQ ID NO:13) and
$R^1$-Arg-$R^2$-$R^3$-norLeu-His-Pro-$R^5$ (SEQ ID NO: 14). In these general formulae $R^1$ is H or Asp; $R^2$ is Val or norLeu; $R^3$ is Tyr, Tyr(PO$_3$)$_2$ or homoSer; $R^4$ is Ile or norLeu; and $R^5$ is H, Phe or Ile.

According to one embodiment, the compound can be any of: Asp-Arg-Val-Tyr(PO$_3$)$_2$-Ile-His-Pro-Phe (SEQ ID NO:4), Asp-Arg-norLeu-Tyr-Ile-His-Pro-Phe (SEQ ID NO:5), Asp-Arg-Val-Tyr-norLeu-His-Pro-Phe (SEQ ID NO:6), Asp-Arg-Val-homoSer-Ile-His-Pro-Phe (SEQ ID NO:7), Arg-norLeu-Tyr-Ile-His-Pro-Phe (SEQ ID NO:9), Arg-Val-Tyr-norLeu-His-Pro-Phe (SEQ ID NO: 10) or Asp-Arg-norLeu-Tyr-Ile-His-Pro (SEQ ID NO:15). According to a different embodiment, position $R^5$ of the general formulae is occupied by a hydrogen moiety. According to another embodiment, the compound is in a matrical or micellar solution. According to another embodiment, the compound is dispersed in the carrier or diluent at a concentration of 1 ng/ml–5,000 μg/ml, or alternatively at a concentration of 10–500 μg/ml, or even at a concentration of 30–200 μg/ml. In a preferred embodiment, the compound is at a concentration of at least 30 μg/ml in the carrier or diluent. According to still another embodiment of the invention, the carrier or diluent can be any one of: a semi-solid polyethylene glycol polymer, carboxymethyl cellulose preparations, crystalloid preparations, viscoelastics or polypropylene glycols. According to certain embodiments, the compound of the invention is disposed on a wound dressing.

Another aspect of the invention relates to a method of accelerating wound healing. This method includes the step of applying to a wound a composition that is useful for accelerating wound healing. This composition includes a suitable carrier or diluent and an amount effective to accelerate wound healing of at least one compound having at least five contiguous amino acids of a general formula that can be any one of:

$R^1$-Arg-norLeu-$R^3$-$R^4$-His-Pro-$R^5$ (SEQ ID NO:11),
$R^1$-Arg-$R^2$-Tyr(PO$_3$)$_2$-$R^4$-His-Pro-$R^5$ (SEQ ID NO:12),
$R^1$-Arg-$R^2$-homoSer-$R^4$-His-Pro-$R^5$ (SEQ ID NO:13) and $R^1$-Arg-$R^2$-$R^3$-norLeu-His-Pro-$R^5$ (SEQ ID NO:14). In these general formulae $R^1$ is H or Asp; $R^2$ is Val or norLeu; $R^3$ is Tyr, Tyr(PO$_3$)$_2$ or homoSer; $R^4$ is Ile or norLeu; and $R^5$ is H, Phe or Ile. According to certain embodiments of the invented method, the compound applied to the wound is any one of: Asp-Arg-Val-Tyr(PO$_3$)$_2$-Ile-His-Pro-Phe (SEQ ID NO:4); Asp-Arg-norLeu-Tyr-Ile-His-Pro-Phe (SEQ ID NO:5); Asp-Arg-Val-Tyr-norLeu-His-Pro-Phe (SEQ ID NO:6); Asp-Arg-Val-homoSer-Ile-His-Pro-Phe (SEQ ID NO:7); Arg-norLeu-Tyr-Ile-His-Pro-Phe (SEQ ID NO:9); Arg-Val-Tyr-norLeu-His-Pro-Phe (SEQ ID NO:10) or Asp-Arg-norLeu-Tyr Ile-His-Pro (SEQ ID NO:15). According to another embodiment of the invention, the compound is applied in a matrical or micellar solution. According to certain embodiments of the invented method, the compound of having the specified general formula is dispersed in a suitable carrier or diluent at a concentration of 1 ng/ml–5,000 µg/ml, or alternatively at 10–500 µg/ml or even at 30–200 µg/ml. In some versions of the invented method, the compound specified by the general formula is at a concentration of at least 30 µg/ml in the carrier or diluent. The carrier or diluent can be semi-solid polyethylene glycol polymer, carboxymethyl cellulose preparations, crystalloid preparations, viscoelastics or polypropylene glycols. In certain embodiments of the invented method, the compound is administered in conjunction with a wound dressing.

BRIEF DESCRIPTION OF THE DRAWINGS

The invention may be better understood with reference to the accompanying drawings, in which.

DETAILED DESCRIPTION OF THE PREFERRED EMBODIMENT

Figure 1:
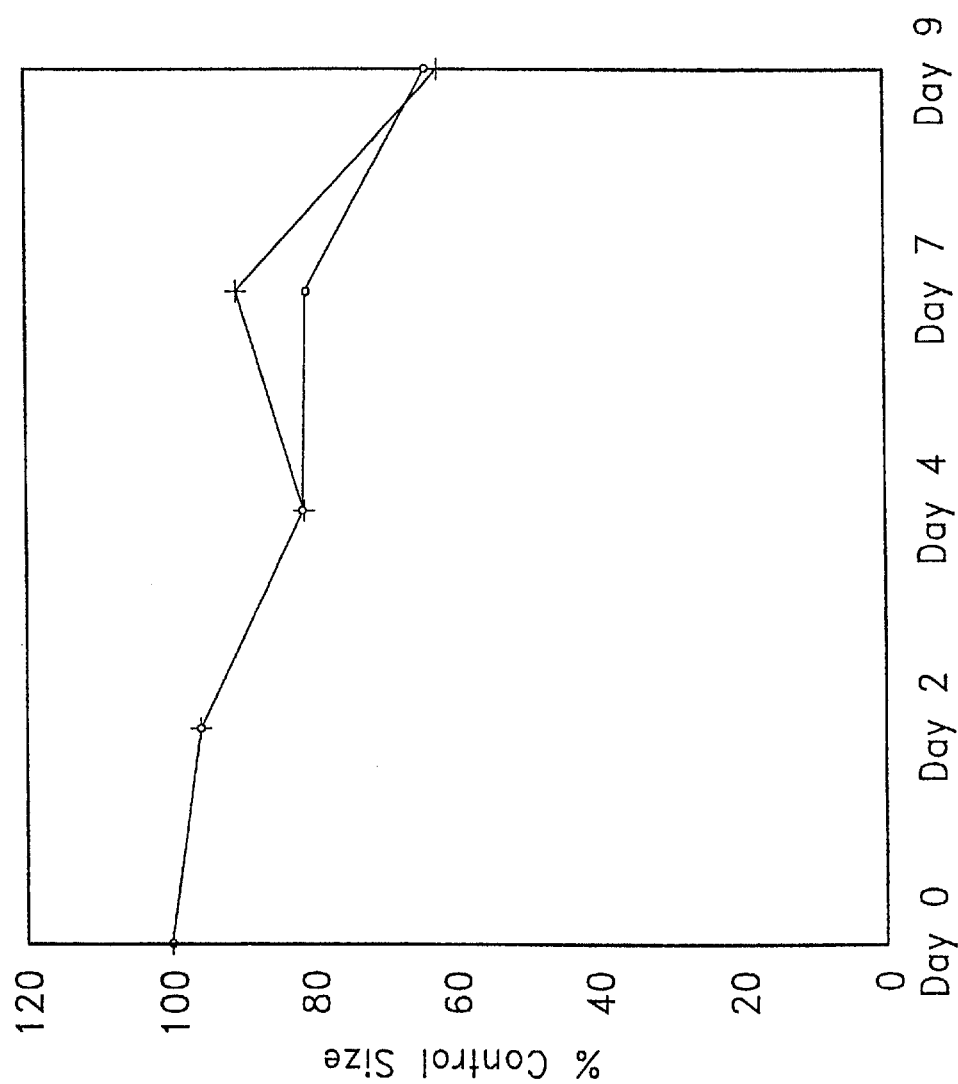
FIG. 1 illustrates the percent of control response in wound closure relative to vehicle-treated controls using AII or (TyrPO$_3$)$_2$$^4$-AII.

Pursuant to the present invention, healing of wounds in mammals is promoted through the use of a composition comprising an effective amount of at least one of the AII analogs disclosed herein. The active agent is generally administered in a matrical or micellar solution and is effective in accelerating re-epithelialization and tissue repair even in very low concentrations.

The active AII analogs and analogs of AII fragments of particular interest in accordance with the present invention are characterized as including a sequence of at least five contiguous amino acids of a general formula which can be any of:

$R^1$-Arg-norLeu-$R^3$-$R^4$-His-Pro-$R^5$ (SEQ ID NO:11),
$R^1$-Arg-$R^2$-Tyr(PO$_3$)$_2$-$R^4$-His-Pro-$R^5$ (SEQ ID NO:12),
$R^1$-Arg-$R^2$ homoSer-$R^4$-His-Pro-$R^1$ (SEQ ID NO:13) and
$R^1$-Arg-$R^2$ $R^3$-norLeu-His-Pro-$R^1$ (SEQ ID NO:14),
wherein $R^1$ is H or Asp;
$R^2$ is selected from the group consisting of Val and norLeu;
$R^3$ is selected from the group consisting of Tyr, Tyr (PO$_3$)$_2$ and homoSer;
$R^4$ is selected from the group consisting of Ile and norLeu; and
$R^5$ is selected from the group consisting of H, Phe and Ile.

Particularly preferred compositions according to the present invention include angiotensin analogs having the sequences presented below in Table 1. Significantly, it is clear that not all fragments or analogs of angiotensin II and angiotensin II fragments possess the wound healing activities which advantageously characterize the invented compositions. For example, AII(6–8), His-Pro-Phe and AII(4–8), Tyr-Ile-His-Pro-Phe (SEQ ID NO:3) have been tested and found not to be effective in accelerating wound healing in our in vivo model system.

Other particularly preferred compositions according to the present invention include analogs of AII(1–7), wherein position Rs in any of SEQ ID NOs:11–14 is occupied by hydrogen. Still other particularly preferred compositions include analogs of AII(3–8), wherein the first two N-terminal positions of the sequences of SEQ ID NOs:11–14 are replaced by hydrogen. Thus, in these latter compositions the amino terminus of the molecule is norLeu or Val. It should be noted that AII(3–8) is also known as "AIV."

In the above formulas, the standard three-letter abbreviations for amino acid residues are employed. In the absence of an indication to the contrary, the L-form of the amino acid is intended.

It has been suggested that AII and its analogs adopt either a gamma or a beta turn [Regoli, D., et al. (1974), Pharmacology of Angiotensin, *Pharmacological Reviews* 26:69]. In general, it is believed that the neutral side chains in positions $R^2$, $R^4$ and Pro at amino acid position seven of the molecule may be involved in maintaining the appropriate distance between the active groups in positions $R^3$, His and $R^5$ residues are primarily responsible for binding to receptors and/or intrinsic activity. Hydrophobic side chains in positions $R^2$, $R^4$ and $R^5$ may also play an important role on the whole conformation of the peptide and/or contribute to formation of a hypothetical hydrophobic pocket.

The side chain of Arg in the second amino acid position of the molecule may contribute to affinity of the compounds for target receptors and/or play an important role in the conformation of the peptide.

For purposes of the present invention, it is believed that $R^2$ may be involved in the formation of linear or nonlinear hydrogen bonds with $R^4$ (in the gamma turn model) or His (in the beta turn model). $R^2$ would also participate in the first turn in a beta antiparallel structure (which has also been proposed as a possible structure). In contrast to other positions in the general formulae presented above, it appears that beta and gamma branching are equally effective in this position. Moreover, a single hydrogen bond may be sufficient to maintain a relatively stable conformation. Accordingly, $R^2$ may suitably be selected from Val and norLeu.

With respect to $R^3$, conformational analyses have suggested that the side chain in this position (as well as in $R^2$ and $R^4$) contribute to a hydrophobic cluster believed to be essential for occupation and stimulation of receptors. Thus, $R^3$ is preferably selected from Tyr, Tyr(PO$_3$)$_2$ and homoSer.

In position $R^4$, an amino acid with a β aliphatic or alicyclic chain is particularly desirable. Therefore, it is preferred that the amino acid in this position be selected from Ile and norLeu.

In the analogs of particular interest in accordance with the present invention, the sixth amino acid position of the molecule is occupied by His. The unique properties of the imidazole ring of histidine (e.g., ionization at physiological pH, ability to act as proton donor or acceptor, aromatic character) are believed to contribute to its particular utility at this position of the molecule. For example, conformational models suggest that His may participate in hydrogen bond formation (in the beta model) or in the second turn of the antiparallel structure by influencing the orientation of Pro at amino acid position seven of the molecule.

In the eighth amino acid position of the molecule, a hydrophobic side chain is particularly useful in binding of the analogs of interest to receptors. Most preferably, $R^5$ is selected from Phe or Ile for the eighth position of the molecule.

As designated below, peptide analogs are identified herein alternatively as analogs of AII or analogs of AII fragments having amino acid substitutions at positions indicated by superscripts. Thus, for example, (TyrPO$_3$)$_2{}^4$-AII is the designation for an AII analog having a (TyrPO$_3$)$_2$ residue substituted at position 4 of AII.

Analogs particularly preferred in the practice of the invention include the following:

TABLE 1

Angiotensin Analogs

| Analog Name | Amino Acid Sequence | Sequence Identifier |
|---|---|---|
| Analog 1 | Asp-Arg-Val-Tyr(PO$_3$)$_2$-Ile-His-Pro-Phe | SEQ ID NO: 4 |
| Analog 2 (GSD-39B) | Asp-Arg-norLeu-Tyr-Ile-His-Pro-Phe | SEQ ID NO: 5 |
| Analog 3 (GSD-40B) | Asp-Arg-Val-Tyr-norLeu-His-Pro-Phe | SEQ ID NO: 6 |
| Analog 4 (GSD-41B) | Asp-Arg-Val-homoSer-Ile-His-Pro-Phe | SEQ ID NO: 7 |
| Analog 5 (GSD-28) | Asp-Arg-Val-Tyr-Ile-His-Pro-Ile | SEQ ID NO: 8 |
| Analog 6 (GSD-39A) | Arg-norLeu-Tyr-Ile-His-Pro-Phe | SEQ ID NO: 9 |
| Analog 7 (GSD-40A) | Arg-Val-Tyr-norLeu-His-Pro-Phe | SEQ ID NO: 10 |
| Analog 8 (9GD) | Asp-Arg-norLeu-Tyr-Ile-His-Pro | SEQ ID NO: 15 |

Angiotensin II is one of the most potent vasoconstrictors known, causing constriction of the small arteries that branch to form the capillaries, i.e., the arterioles. The biological formation of angiotensin is initiated by the action of renin on the plasma substrate angiotensinogen. The substance so formed is a decapeptide called angiotensin I which is converted to angiotensin II by the converting enzyme angiotensinase that removes the C-terminal His-Leu residues from angiotensin I.

Studies have shown that the vasoactive product of the renin-angiotensin system, AII increases the release of growth factors, mitogenesis, chemotaxis and the release of extracellular matrices of cultured cells that are involved in wound repair [Dzau, V. E., et al. (1989), Molecular mechanism of angiotensin in the regulation of vascular and cardiac growth, *J. Mol. Cell Cardiol.* 21 (Supple III):S7; Berk, B. C., et al. (1989), Angiotensin II stimulated protein synthesis in cultured vascular smooth muscle cells, *Hypertension* 13:305–14; Kawahara, Y., et al. (1988), Angiotensin II induces expression of the c-fos gene through protein kinase C activation and calcium ion mobilization in cultured vascular smooth muscle cells, *BBRC* 150:52–9; Naftilan, A. J., et al. (1989), Induction of platelet-derived growth factor A-chain and c-myc gene expressions by angiotensin II in cultured rat vascular smooth muscle cells, *J. Clin. Invest.* 83:1419–24; Taubman, M. B., et al. (1989), Angiotensin II induces c-fos mRNA in aortic smooth muscle, Role of Ca$^{2+}$ mobilization and protein kinase C activation, *J. Biol. Chem.* 264:526–530; Nakahara, K., et al. (1992), Identification of three types of PDGF-A chain gene transcripts in rabbit vascular smooth muscle and their regulated expression during development and by angiotensin II, *BBRC* 184:811–8; Stouffer, G. A. and G. K. Owens (1992), Angiotensin II induced mitogenesis of spontaneously hypertensive rat derived cultured smooth muscle cells is dependent on autocrine production of transforming growth factor-β, *Circ. Res.* 70:820; Wolf, G., et al. (1992), Angiotensin II stimulates the proliferation and biosynthesis of type I collagen in cultured marine mesangial cells, *Am. J. Pathol.* 140:95–107; Bell, L. and J. A. Madri (1990), Influence of the angiotensin system on endothelial and smooth muscle cell migration, *Am. J. Pathol.* 137:7–12]. In addition, AII was shown to be angiogenic in rabbit corneal eye and chick chorioallantoic membrane models (Fernandez, L. A., et al. (1985), Neovascularization produced by angiotensin II, *J. Lab. Clin. Med.* 105:141; LeNoble, F. A. C., et al. (1991), Angiotensin II. stimulates angiogenesis in the chorio-allantoic membrane of the chick embryo, *Eur. J. Pharmacol.* 195:305–6]. Therefore, AII may accelerate wound repair through increased neovascularization, growth factor release, reepithelialization and production of extracellular matrix.

Through an increase in the flow of blood and nutrients to an injured tissue, AII may increase the rate of wound repair. AII may also accelerate wound repair through the generation of growth factors at the site of injury. Exogenous addition of growth factors has been shown to accelerate wound repair through a variety of mechanisms [Grotendorst, G. R., et al. (1985), Stimulation of granulation tissue formation by platelet-derived growth factor in normal and diabetic rats, *J. Clin. Invest.* 76:2323–9; Mustoe, T. A., et al. (1987), Accelerated healing of incisional wounds in rats induced by transforming growth factor-β, *Science* 237:1333–5; Pierce, G. F., et al. (1988), In vivo incisional wound healing augmented by platelet-derived growth factor and recombinant c-sis gene homodimeric proteins, *J. Exp. Med.* 167:974–87; Lynch, S. E., et al. (1989), Growth factors in wound healing, *J. Clin. Invest.* 84:640–6; Greenhalgh, D. G., et al. (1990), PDGF and FGF simulate wound healing in the genetically diabetic mouse, *Am. J. Pathol.* 136:1235–46]. Recent studies showed that AII increased neointima formation in the carotid artery and aorta after injury [Powell, J. S., et al. (1989), Inhibitors of angiotensin-converting enzyme prevent myointimal proliferation after vascular injury, *Science* 245:186–8; Powell, J. S., et al. (1991), The proliferative response to vascular injury is suppressed by converting enzyme inhibition, *J. Cardiovasc. Pharmacol.* 16 (suppl 4):S42–9; Capron, L., et al. (1991), Effect of ramipril, an inhibitor of angiotensin converting enzyme, on the response of rat thoracic aorta to injury with a balloon catheter, *J. Cardiovasc. Pharmacol.* 18:207–11; Osterriedes, W., et al. (1991), Role of angiotensin II injury-induced neointima formation in rats, *Hypertension* 18:Suppl II60–64; Daemen, M. J. A. P., et al. (1991), Angiotensin II induces smooth muscle cell proliferation in the normal and injured rat arterial wall, *Circ. Res.* 68:450–6]. As a result of these observations, studies were conducted to determine the mechanism by which endogenous AII may induce intimal hyperplasia. AII was shown to act as a mitogen for smooth muscle cells, fibroblasts and endothelial cells [Schelling, P., et al. (1979), Effects of angiotensin II and angiotensin II antagonist saralysin on cell growth and renin in 3T3 and SV3T3 cells, *J. Cell. Physiol.* 98:503–13; Campbell-Boswell, M. and A. L. Robertson (1981), Effects of angiotensin II and vasopressin on human smooth muscle cells in vitro, *Exp. Mol. Pathol.* 35:265–76; Emmett, N., et al. (1986), Effect of saralasin (angiotensin II antagonist) on 3T3 cell growth and proliferation, *J. Cell. Biol.* 103:171 (Abst); Paquet, J. L., et al. (1990), Angiotensin II-induced proliferation of aortic myocytes in spontaneously hypertensive rats, *J. Hypertens.* 8:565–72; Dzau, et al., supra]. AII also increased the protein content and size of vascular smooth muscle cells [Berk, et al. (1989), supra; Geisterfer, A. A. T., et al. (1988), Angiotensin II induces hypertrophy, not hyperplasia, of cultured rat aortic smooth muscle cells, *Cir. Res.* 62:749–56]. Studies showed that AII increases the release of growth factors of various types, including PDGF, heparin-binding EGF and transforming growth factor-β (TGFβ), and growth-related proto-oncogenes from smooth muscle cells, endothelial cells and cardiac fibroblasts [Kawahara, et al. (1988), supra; Naftilan, A. J. (1992), The role of angiotensin II in vascular smooth muscle cell growth, *J. Cardiovas. Pharmacol.* 20:S37–40; Naftilan, et al. (1989), supra; Taubman, et al. (1989), supra; Nakahara, et al. (1992), supra; Temizer, et al. (1992), supra; Gibbons, G. H., et al. (1992), Vascular smooth muscle cell hypertrophy vs hyperplasia, Autocrine transforming growth factor-beta 1 expression determines growth response to angiotensin II, *J. Clin. Invest.* 90:456–61; Bell, L., et al. (1992), Autocrine angiotensin system regulation of bovine aortic endothelial cell migration and plasminogen activator involves modulation of proto-oncogene pp6Oc-src expression, *J. Clin. Invest.* 89:315–20; Stouffer and Owens (1992), supra]. The hypertrophy of vascular smooth muscle cells by AII was mediated through PDGF [Berk, B. C. and G. N. Rao (1993), Angiotensin II-induced vascular smooth muscle cell hypertrophy: PDGF A-chain mediates the increase in size, *J. Cell. Physiol.* 154:368–80].

Therefore, it is conceivable that AII acts to accelerate wound repair through increasing the levels of these growth factors in the wound tissue. Additionally, AII was shown to stimulate collagen synthesis thereby suggesting a role for this factor in extracellular matrix formation [Wolf, G., et al. (1991), Intracellular signalling of transcription and secretion of type IV collagen after angiotensin II-induced cellular hypertrophy in cultured proximal tubular cells, *Cell. Reg.* 2:219–27; Wolf, et al. (1992), supra; Zhou, G., et al. (1992), Angiotensin II mediated stimulation of collagen synthesis in cultured cardiac fibroblasts, *FASEB. J.* 6:A1914]. Wound repair also involves chemotaxis of the necessary cell types into the wound bed. AII was also shown to induce the migration of endothelial cells and smooth muscle cells in vitro [Bell and Madri (1990), supra].

Recent studies also have indicated that expression of AII receptors is altered during the process of wound repair [Viswanathan, M., and J. M. Saavedra (1992), Expression of Angiotensin II $AT_2$ Receptors in the Rat Skin During Experimental Wound Healing, *Peptides* 13:783–6; Kirnura, B., et al. (1992), Changes in skin angiotensin II receptors in rats during wound healing, *BBRC* 187:1083–1090]. These changes, along with evidence of an increase in the local production of AII at the site of repair suggests that AII may play a key role in the process of wound repair.

The actions of AII that may be involved in wound repair have recently been reviewed [Phillips et al. 1994. Angiotensin receptor stimulation of transforming growth factor-β in rat skin and wound healing. In Angiotensin Receptors (ed J M Saavedra and PBMWM Timmermans), Plenum Press, New York, N.Y., pp 377–396]. In the majority of studies reported, these effects have been shown to be mediated by the AT1 receptor.

The blood pressure effects (and most other effects, such as aldosterone secretion and increased thirst) of AII are mediated by the type 1 receptor (AT1 receptor) [Wong, P C 1994. Angiotensin antagonists in models of hypertension. In: Angiotensin Receptors (J M Saavedra and PBMWM Tirnmermans), Plenum Press N.Y., N.Y. pp 319–336; MacKenzie et al. 1994. TCV 116 prevents progressive renal injury in rats with extensive renal ablation. J. Hypertension 12 (Suppl 9): S11–S16; Gupta, et al. 1995. Locally generated angiotensin II in the adrenal gland regulates basal, corticotropin and potassium-stimulated aldosterone secretion. Hypertension 25:443–448; Liorens-Cortes, et al. 1994. Tissue expression and regulation of type 1 angiotensin II receptor subtypes by quantitative reverse transcriptase-polymerase chain reaction analysis. Hypertension 24:538–548; Wong, et al. 1992. Enhancement of losartan (Dup 753)-induced angiotensin II receptor antagonism by PD 123177 in rats. Eur J Pharmacol 220:267–70]. This conclusion is based upon the blocking of the action of AII by receptor subtype specific antagonists.

The effects of AII and AII antagonists have been examined in two experimental models of vascular injury and repair. Studies have been mixed with regards to the contribution of AT2 to hyperplasia of vessels after balloon injury to the vasculature. In the rat carotid artery, the majority of receptors are AT2 [Pratt, R E et al. 1992. The AT2 isoforms of the angiotensin receptor mediates myointimal hyperplasia following vascular injury. Hypertension 20:432]. By contrast, neointimnal cells of the injured rat thoracic aorta express predominately AT1 receptors. [Viswanathan, M et al. Balloon angioplasty enhances the expression of angiotensin II subtype AT1 receptors in the neointima of rat aorta. J Clin Invest 90:1707–12, 1992]. Treatment of rats with PD 123319 (AT2 specific antagonist) reduced intimal hyperplasia by 73% while losartan (AT1 specific antagonist) decreased intimal area by 95% [Pratt et al. (1992), supra]. In a similar model, CGP 42112 (AT2 antagonist) infused perivascularly for 14 days prevented neointimal formation, but low doses of losartan were ineffective [Janiak et al. 1992. Role of angiotensin subtype 2 receptor in neointima formation after vascular injury. Hypertension 20:737–45]. In other studies, losartan at higher doses was found to be effective [Forney Prescott et al. 1991. Angiotensin-converting enzyme inhibitor versus angiotensin II, AT1 receptor antagonist. Effect on smooth muscle cell migration and proliferation after balloon catheter injury. Am J Pathol 139:1291–6; Kauffinan, et al. 1991. Losartan, a nonpeptide angiotensin II (Ang II) receptor antagonist, inhibits neointima formation following balloon injury to rat carotid arteries. Life Sci 49:223–228]. Therefore, it is conceivable that both receptor subtypes may play a role in the formation of vascular lesions after balloon injury.

During experimental wound healing in young animals, the expression of AII receptors increase significantly in a localized band of tissue within the superficial dermis of the skin surrounding the wound; the major proportion of the increase is due to AT2 receptor [Viswanathan et al. 1992. Expression of angiotensin II AT2 receptors in the rat skin during experimental wound healing. Peptides 13:783–6; Kimura et al. Changes in skin angiotensin II receptors in rats during wound healing. Biochem Biophys Res Commun 187:1083–90]. These studies were done in adult rats (as are used in the experiments reported herein), AT1 receptors are altered after an incisional wound. The experimental designs in these latter studies do not distinguish between the dermis and other portions of the wound.

Many studies have focused on AII(1–7) to evaluate its activity. Many of the effects of AII(1–7) are attributed to acting through the AT2 receptor. However, this is not consistent and depends upon the tissue examined.

AII(1–7) does not have many of the effects of AII. AII(1–7) lacks pressor activity or has very mild (effective at 10,000–100,000 times the dose of AII) effects on blood pressure depending upon the model tested and route of administration. In fact, AII(1–7) has a depressor effect on blood pressure that may be mediated through prostanoid synthesis. In addition, in contrast to the effects of AII, AII(1–7) does not cause catecholamine release and aldosterone release and is not dipsogenic [Webb, et al. 1992, Molecular characterization of angiotensin II type II receptors in rat pheochromocytoma cells, *Peptides* 13:499–508; Cheng, et al. (1994), Comparison of pressor responses to angiotensin I, II and III in pulmonary vascular bed of cats, *Am. J. Physiol.* 266:H2247–H2255; Moriguchi, A., et al. (1994), Differential regulation of central vasopressin in transg enic rats harboring the mouse Ren-2 gene, *Am. J. Physiol.* 267:R786–R791; Schiavone, et al. (1990), Angiotensin-[1–7]: Evidence for novel actions in the brain, *J. Cardiovascular Pharmacol.* 16(Suppl. 4):S19–S24; Ferrario, et al. (1991), Angiotensin-(1–7): A new hormone of the angiotensin system, *Hypertension* 19[suppl. III]:III-126–III-133].

In one report, AII(1–7) is a weak pressor that requires about 10,000 times more AII(1–7) than AII to get a comparable response [Benter, et al. (1993), Cardiovascular actions of angiotensin(1–7), *Peptides* 14:679–684]. In this system, AII(1–7) had a long depressor effect that was dose dependent. AII(3–7) had less of a pressor effect than AII (1–7), but had no depressor effect. It is also noted that AII(1–7), AII(2–7) and AII(3–7) may affect the dopamine system and memory.

In several systems, the actions of AII(1–7) are quite distinct from AII. AII stimulates choline production in rat mesangial cells through the AT1 receptor; AII(1–7) and AII(1–6) has very weak effects on this parameter [Pfeilschifter, et al. (1992), Angiotensin II stimulation of phospholipase D in rat renal mesangial cells is mediated by the AT1 receptor subtype, *Eur. J. Pharmacol.* 225:57–62].

In porcine aortic endothelial cells, AI and AII(1–7) stimulated the release of prostaglandin E2 and I2, but AII did not have this effect [Jaiswal, et al. (1992), Stimulation of endothelial cells prostaglandin production by angiotensin peptides, Characterization of receptors, *Hypertension* 19 (Suppl II):11–49–II–55]. AII is able to stimulate the release of prostanoids in other cells types and in intact blood vessels but not human or porcine endothelial cells. The effect on endothelial cells was through a receptor distinct from AT1 and AT2.

In rat glomerulus preparations, AII inhibited the formation of cAMP in response to histamine, serotonin and parathyroid hormone through the AT1 receptor [Edwards, R. M. and E. J. Stack (1993), Angiotensin II inhibits glomerular adenylate cyclase via the angiotensin II receptor subtype 1 (AT1), *J. Pharmacol. Exper. Ther.* 266:506–510]. AII(1–7) did not have this effect.

In porcine vascular smooth muscle cells and human astrocytes, AII and AI(1–7) increases prostaglandin release; only angiotensin II increases the release of intracellular $Ca^{2+}$ [Jaiswal, et al. (1993), Differential regulation by angiotensin peptides in porcine aortic smooth muscle cells: subtypes of angiotensin receptors involved, *J. Pharmacol. and Exp. Therapeutic* 265:664–673; Jaiswal, et al. (1991), Subtype 2 angiotensin receptors mediate prostaglandin synthesis in human astrocytes, *Hypertension* 17:1115–1120].

AII(1–7) dilates porcine coronary artery rings, perhaps through nitric oxide [Porsti, et al. (1994), Release of nitric oxide by angiotensin-(1–7) from porcine coronary endothelium: implications for a novel angiotensin receptor, *Br. J. Pharmacol.* 111:652–654]. This was not observed with AII, AIII or AII(3–8). This effect was not attenuated by antagonists of AT1 or AT2 receptors, AII causes depolarization of rat isolated nodose ganglion; AII(1–7) does not [Widdop, et al. (1992), Electrophysiological responses of angiotensin peptides on the rat isolated nodose ganglion, *Clin. and Exper. Hyper-Theory and Practice* A14:597–613]. Indeed, AII(1–7) may have novel actions on brain function [Schiavone, et al. (1990), Angiotensin-[1–7]: Evidence for novel actions in the brain, *J. Cardiovascular Pharmacol.* 16(Suppl 4):S19–S24].

There are activities that AII(1–7) shares with AII, such as release of vasopressin and modulation of phospholipase A2 activity in proximal tubule cells [Andreatta-Van Leyen, S., et al. (1993), Modulation of phospholipase A2 activity and sodium transport by angiotensin-(1–7), *Kidney International* 44:932–6; Moriguchi, A., et al. (1994), Differential regulation of central vasopressin in transgenic rats harboring the mouse Ren-2 gene, *Am. J. Physiol.* 267: R786–R791; Ferrario, et al. (1991), Angiotensin-(1–7): A new hormone of the angiotensin system, *Hypertension* 19[suppl III]:III- 126–III-133]. These activities, however, are likely not involved in wound repair.

The effects of other fragments of AII have been studied in very few instances. Most neurons in the paraventricular nucleus are excited by Ang(1–7), AII and AIII, but AII(1–7) is weaker in this effect; in many neurons, AII(2–7) was inactive [Ambuhl, et al. (1992), Effects of angiotensin analogues and angiotensin receptor antagonists on paraventricular neurones, *Regulatory Peptides* 38:111–120]. AII injected in the lateral cerebral ventricle increased the motility, stereotypy and learning of conditioned avoidance responses; AII(1–6) and AII(2–6) were not active in these psychotropic activities [Holy, Z., et al. (1993), *Polish J. Pharmacol.* 45:31–41].

AII(4–8), AII(5–8) and AII(1–4) showed only a slight effect on water intake when injected into the anterior diencephalon in the rat, and AII(1–7) was completely inactive [Fitzsimmons, J. T. (1971), The effect on drinking of peptide precursors and of shorter chain peptide fragments of angiotensin II injected into the rat's diencephalon, *J. Physiol.* 214:295–303]. Intracerebroventricular infusion of AII fragments [AII(4–8) and AII(5–8)] in the rat produced a minimal effect on blood pressure even when given at concentrations 1,000 times higher than that of AII that increased blood pressure [Wright, et al. (1989), Structure-function analyses of brain angiotensin control of pressor action in rats, *Am. J. Physiol.* 257:R1551–R1557]. In both of these studies, the fragments were injected directly into the brain; this is highly artificial and does not allow for systemic metabolism.

According to the method of the invention, one or more of the active AII analogs disclosed herein is applied to wound tissue in amounts sufficient to increase the healing rate of tissue. These compounds can significantly accelerate the rate of healing at nanomolar levels in vivo. For any given active agent, the optimum concentration for a given formulation may readily be determined empirically using no more than routine experimentation. In general, an amount of active agent suitable for use in accordance with the present invention ranges from about 0.001 $\mu$g to about 10 mg per kilogram body weight.

The compounds of the invention may be applied in a variety of solutions. Suitable solutions for use in accordance with the present invention are sterile, dissolve sufficient amounts of the peptide, and are not harmful to wound tissue. In this regard, the compounds of the present invention are very stable but are hydrolyzed by strong acids and bases. The compounds of the present invention are soluble in organic solvents and in aqueous solutions at pH 5–8.

Any type of application means may be employed which permits the influx of the active agents into the tissue over a period of time. For example, an aqueous solution could be applied to the wound tissue through a gauze bandage or strip, or such a solution could be formulated so that a timed perfusion may be obtained (using, e.g., liposomes, ointments, micelles, etc.). Methods for the production of these formulations with the compounds of the present invention are apparent to those of ordinary skill in the art. The particular concentration of active agent employed is not critical, as the tissue-repairing effect is obtainable even when the compounds are present in nanomolar quantities.

Preferably, a matrical or micellar solution is employed with the active agent present in a concentration range of from 1 ng/ml–5,000 $\mu$g/ml, from 10–500 $\mu$g/ml or 30–500 $\mu$g/ml. A preferred concentration range that is convenient will be at least 30 $\mu$g/ml. A particular matrical solution which has been used to advantage in the described Examples is a semi-solid polyethylene glycol polymer sold under the trademark HYDRON by Hydro Med Sciences, New Brunswick, N.J. Another preferred solution is a micellar solution sold under the trade name PLURONICS F108 by BASF, Ludwigshafen, Germany. Under room temperature conditions, this solution is a liquid, but when applied to warm tissue the solution forms a gel which permits the infusion of active agent into the wound tissue for a period of several days. Other preferred formulations include carboxymethyl cellulose preparations, crystalloid preparations (e.g., saline, Ringer's lactate solution, phosphate-buffered saline, etc.), viscoelastics, polyethylene glycols, polypropylene glycols and wound dressings (e.g., bandages, etc.).

The healing effects of the compounds of the present invention may be provided in a variety of instances. The solution may be applied topically to surface wound tissue in the treatment of ulcers, lesions, injuries, diabetic ulcers, burns, trauma, stasis ulcers, periodontal conditions, lacerations and other conditions. In addition, intraperitoneal wound tissue such as that resulting from invasive surgery may be treated with a composition in accordance with the present invention to accelerate healing. For example, following the surgical removal of a colon section or other tissue, the surgical plane may be coated with a solution of active agent prior to closing the surgical site in order to accelerate internal capillary perfusion and healing. In addition, the rate of localized healing may be increased by the subdermal administration of active agent by injection or otherwise.

Analogs of angiotensin II and analogs of angiotensin II fragments having the structures disclosed herein were prepared using an automated peptide synthesizer and methods familiar to those having ordinary skill in the art. Each of the analogs was tested for its ability to accelerate wound healing according to the method described below. Results of procedures were used to determine the extent of wound closure at days 2, 4, 7 and 9, measured as a percentage of a vehicle-treated control wound. Since all of the analogs were not tested during the same experimental procedure, AII was included as a positive control for each group of peptides tested.

The invention may be better understood with reference to the accompanying Examples, which are intended for purposes of illustration only and should not be construed as in any sense limiting the scope of the invention, as defined in the claims appended hereto. The experimental results presented below establish the general utility of the invented compositions for accelerating wound healing.

The following Example describes the methods used to demonstrate that angiotensin analogs having the structures disclosed herein exhibited unexpectedly good activity in an in vivo wound healing assay.

EXAMPLE 1

Use of Wound Healing Compositions

Female Sprague Dawley rats, 12 weeks old, were obtained from Simonsen Laboratories, Gilroy, Calif. On the day of surgery, the rats received intramuscular ketamine/rompum anesthesia prior to preparation for surgery. The rats were shaved and scrubbed with betadine. Two 1.5×1.5 cm full thickness dermal wounds were created on the dorsal surface of the rat. Following excision of the skin, the size of the wound was outlined on a glass slide, and the medicament was administered in 100 $\mu$l of 10% carboxymethyl cellulose in 0.05 M phosphate buffer (pH 7.2). The test materials were administered in a randomized fashion; all materials were tested at 100 $\mu$g/wound. Controls were treated with vehicle only. After administration of the materials, the rats were bandaged and allowed to recover from anesthesia. The medicaments were administered daily for the first five days after surgery. At days 2, 4, 7 and 9, the area of the skin wounds was measured under methoxyflurane anesthesia (commercially available as Metofane from Pittman-Moore, Mundelein, Ill.). The area of the wound was determined by (1) tracing the wound shape onto graph paper (1×1 mm squares); (2) cutting out the shape; (3) weighing the paper and comparing the weight with a 1.5×1.5 cm paper cutout; and (4) counting the number of squares. In addition, on days 2 and 4 the area of granulation tissue was similarly determined.

Figure 2:
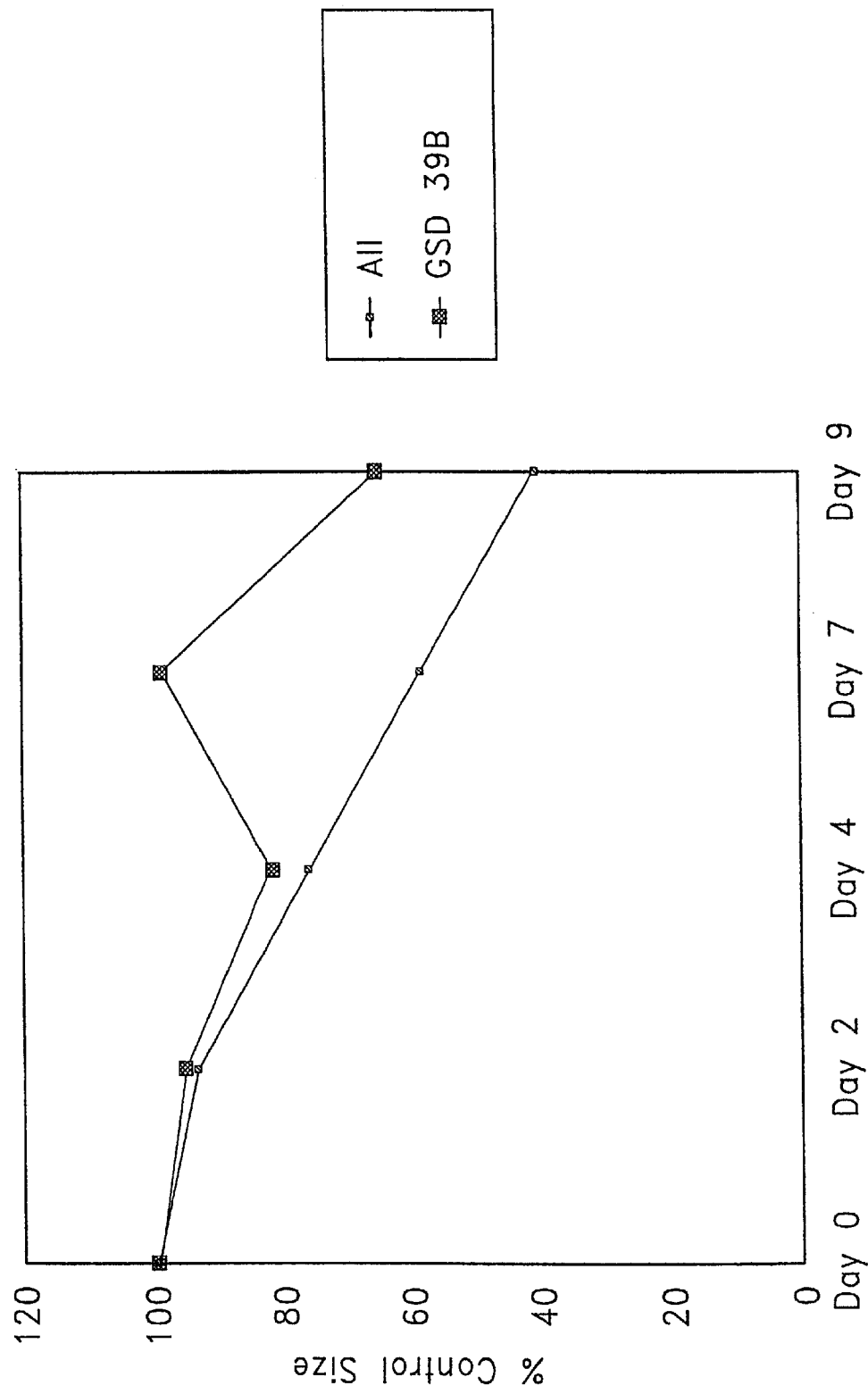
FIG. 2 illustrates the percent of control response in wound closure relative to vehicle-treated controls using AII or the analog GSD-39B.
Figure 3:
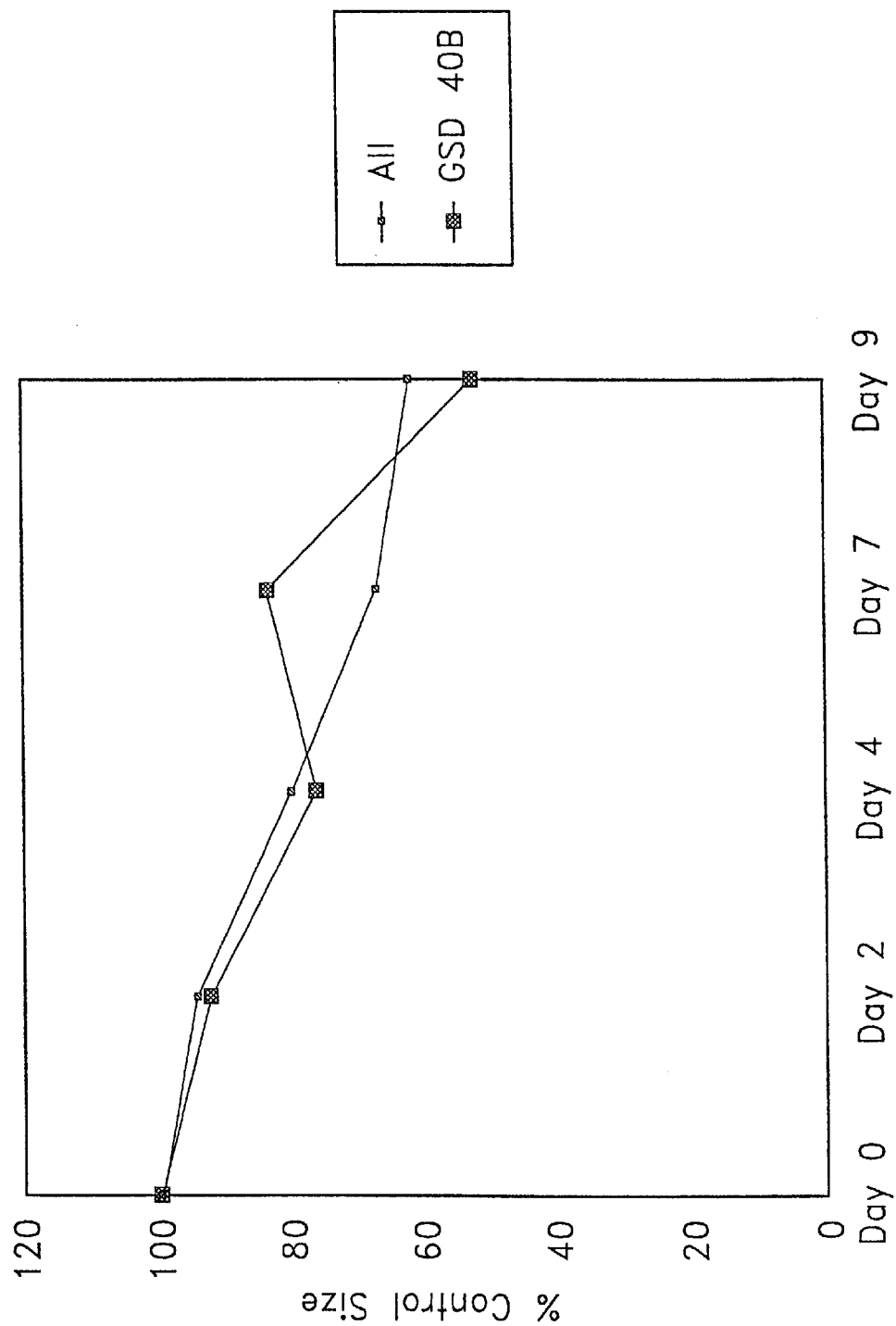
FIG. 3 illustrates the percent of control response in wound closure relative to vehicle-treated controls using AII or the analog GSD-40B.
Figure 4:
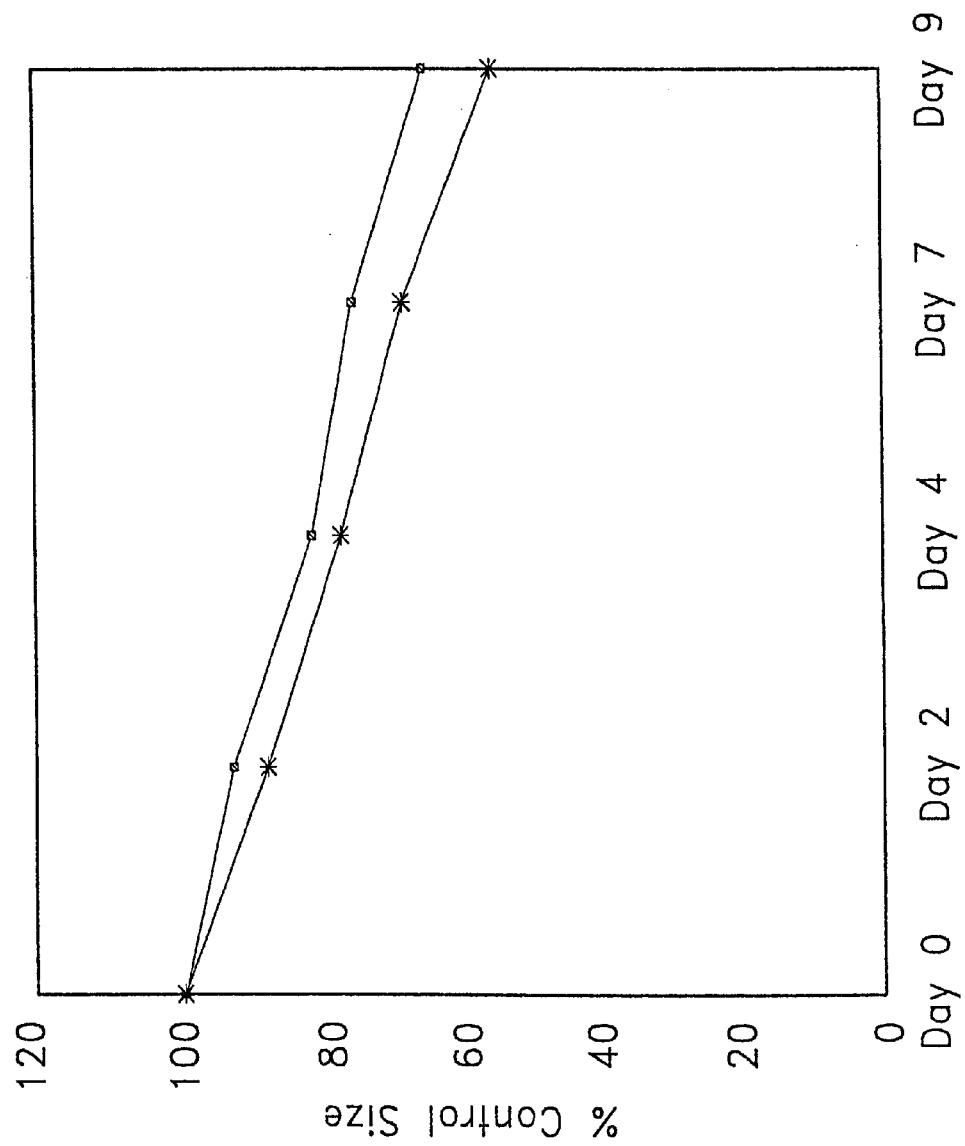
FIG. 4 illustrates the percent of control response in wound closure relative to vehicle-treated controls using AII or the analog GSD-41B.
Figure 5:
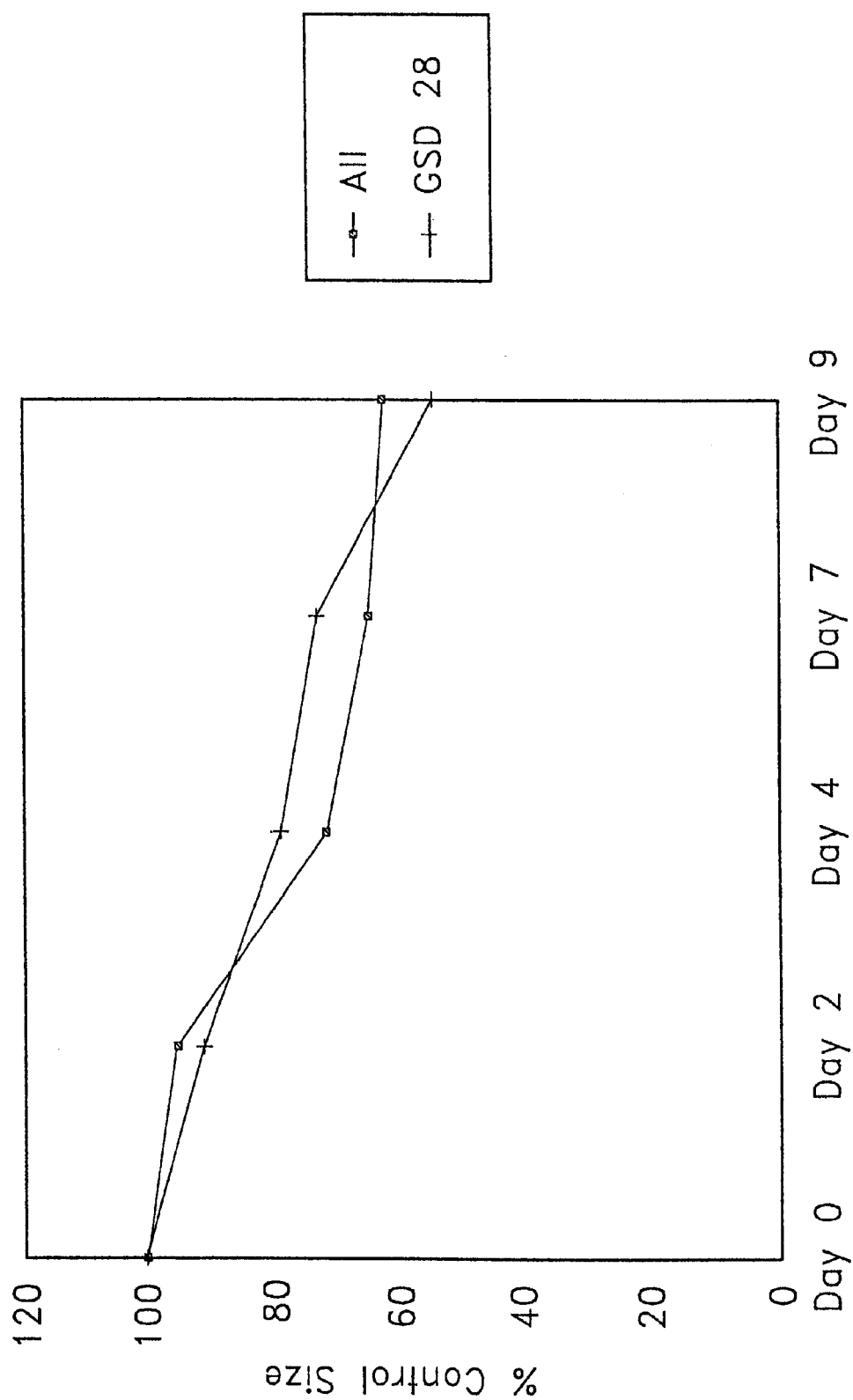
FIG. 5 illustrates the percent of control response in wound closure relative to vehicle-treated controls using AII or the analog GSD-28.
Figure 6:
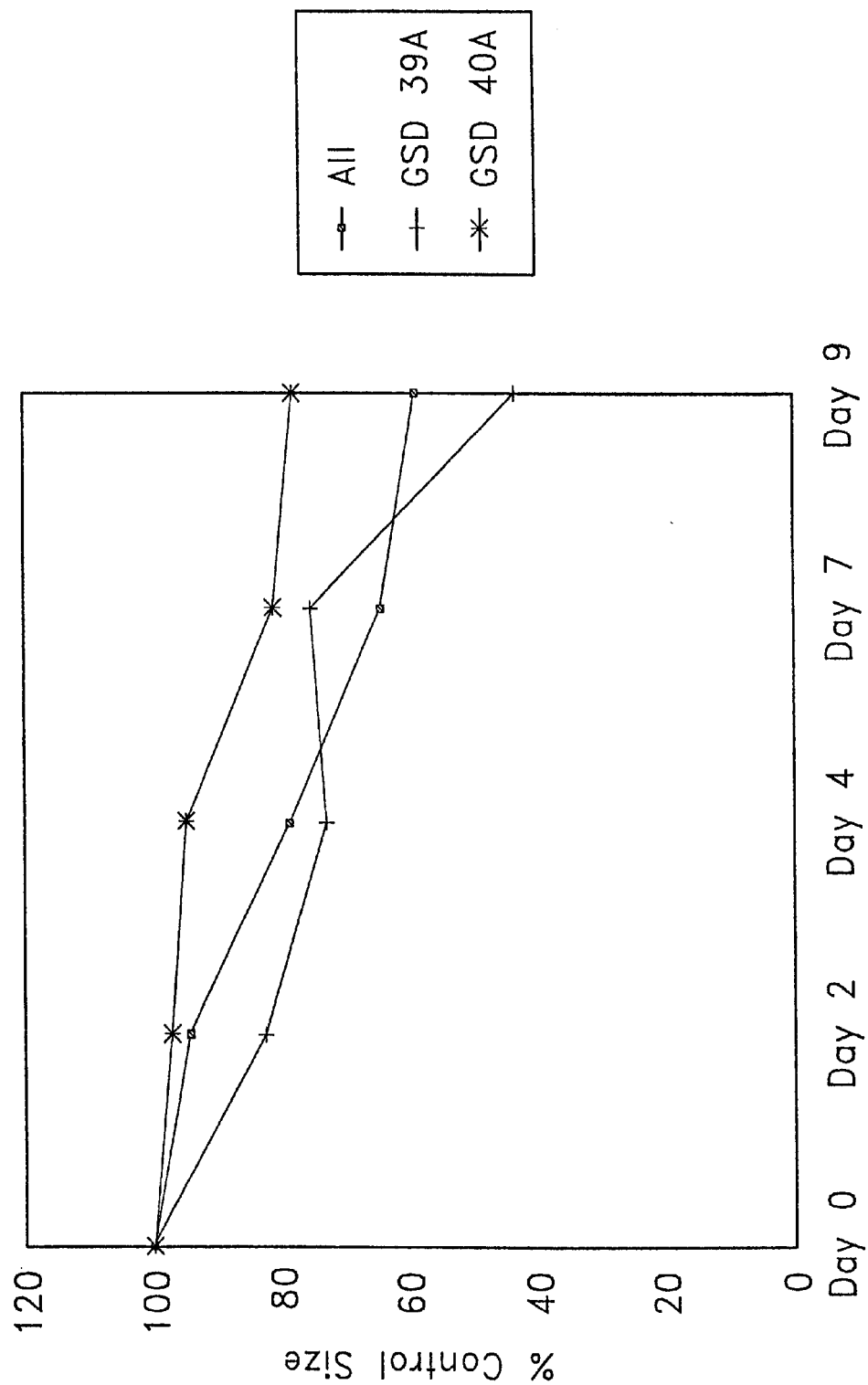
FIG. 6 illustrates the percent of control response in wound closure relative to vehicle-treated controls using AII or the analogs GSD-39A and GSD-40A.
Figure 7:
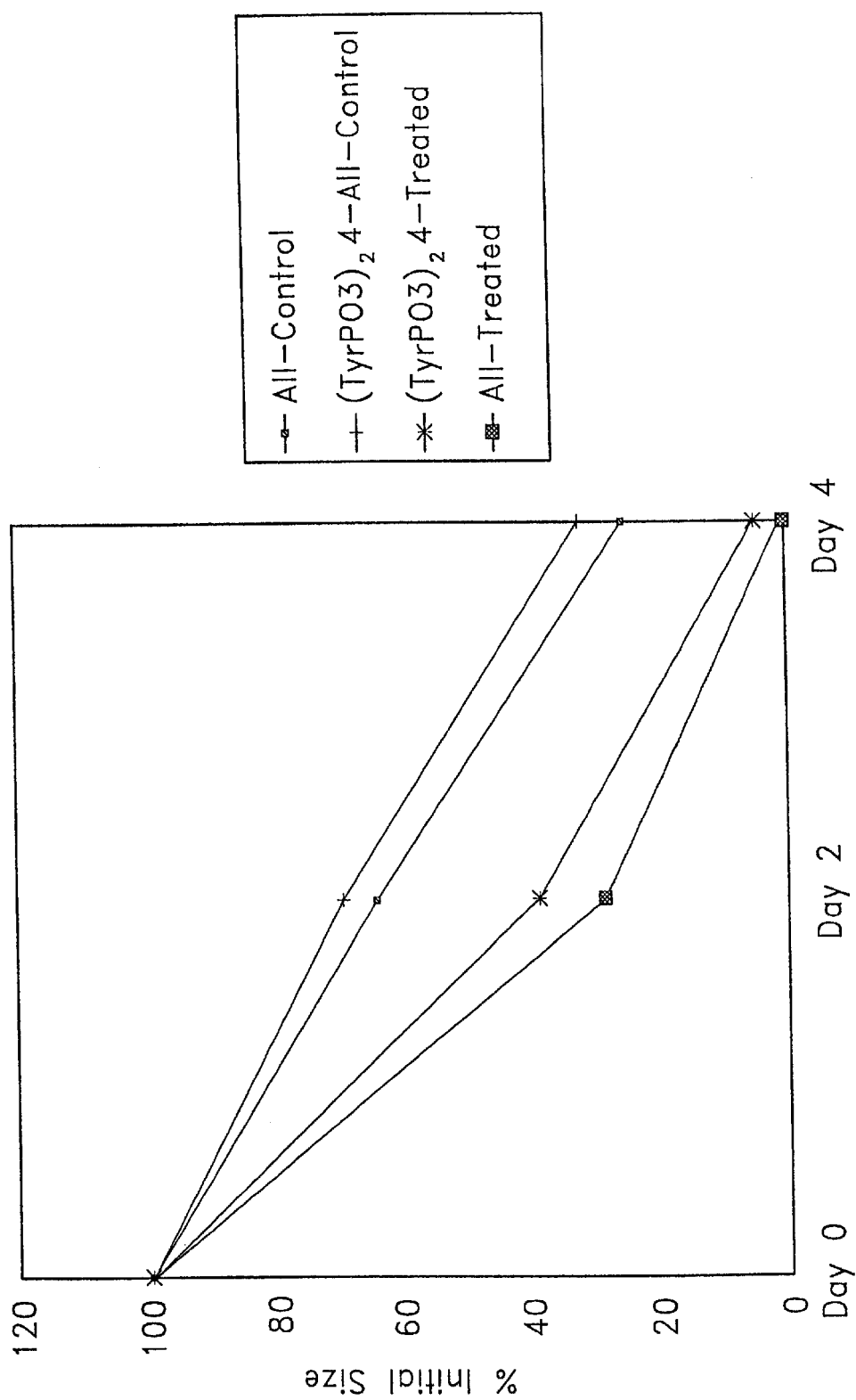
FIG. 7 illustrates the percentage change in size of granulation tissue for control and test wounds treated either with AII or (TyrPO$_3$)$_2$$^4$-AII.
Figure 8:
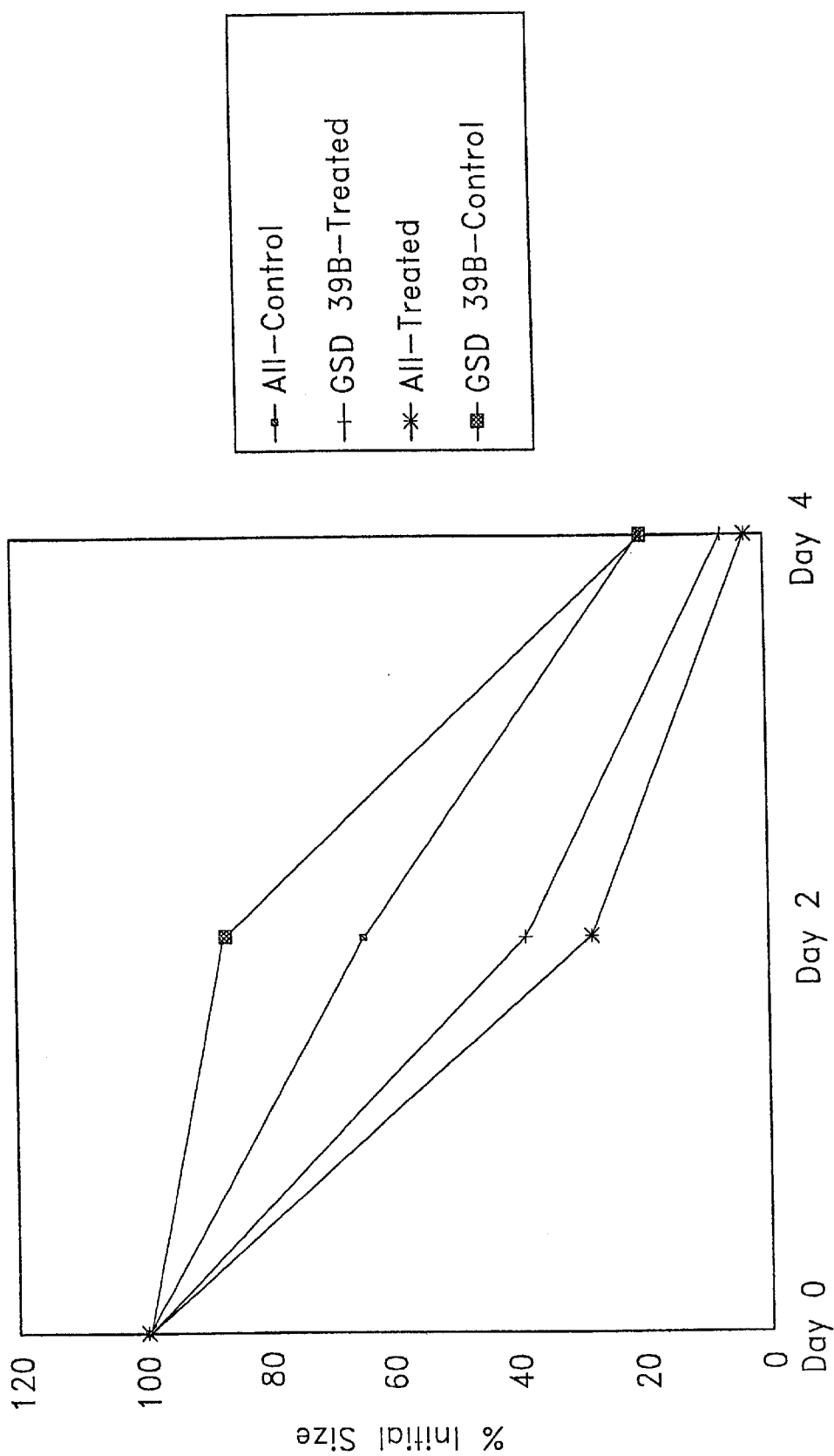
FIG. 8 illustrates the percentage change in size of granulation tissue for control and test wounds treated either with AII or the analog GSD-39B.
Figure 9:
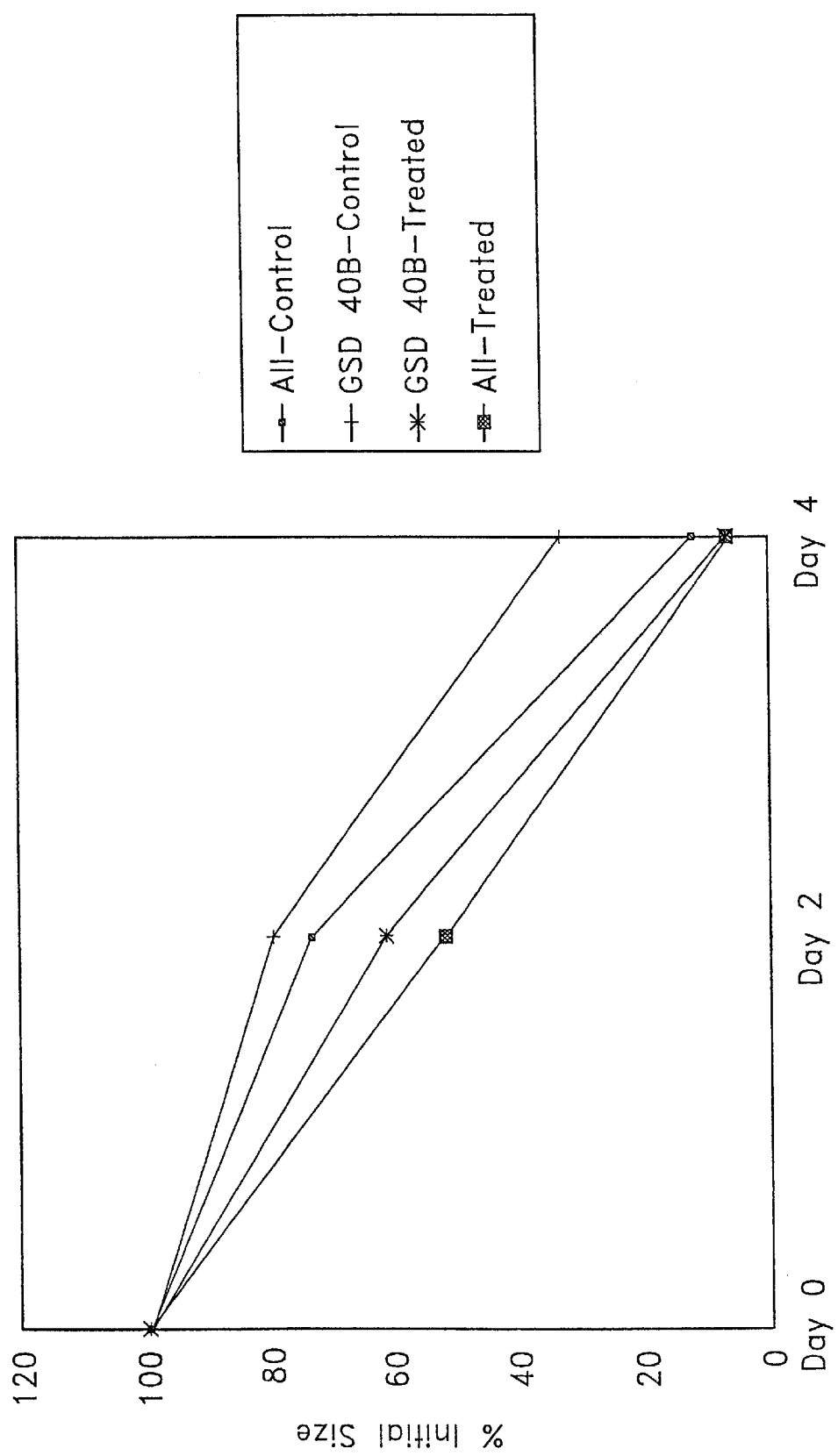
FIG. 9 illustrates the percentage change in size of granulation tissue for control and test wounds treated either with AII or the analog GSD-40B.
Figure 10:
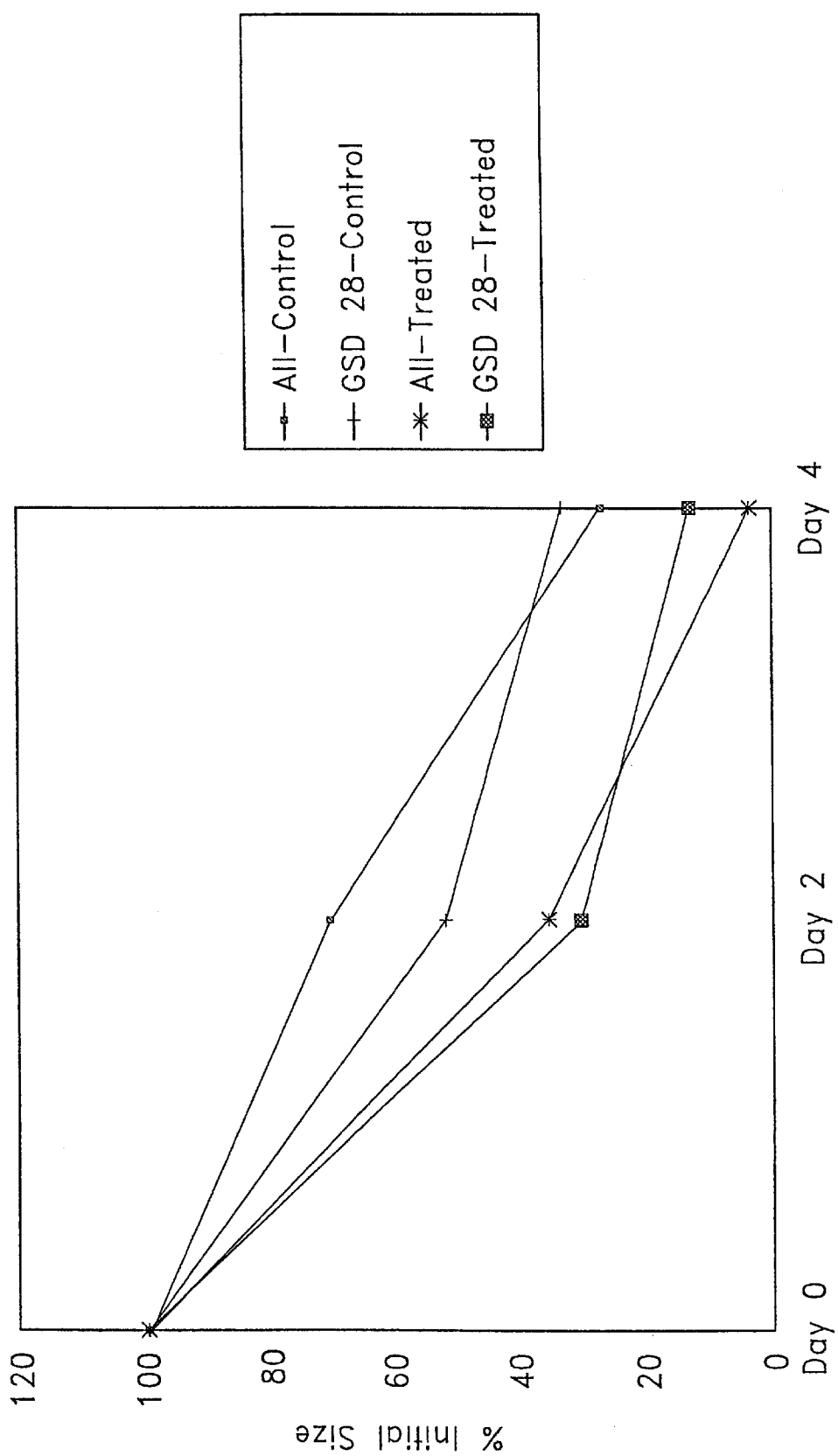
FIG. 10 illustrates the percentage change in size of granulation tissue for control and test wounds treated either with AII or the analog GSD-28.
Figure 11:
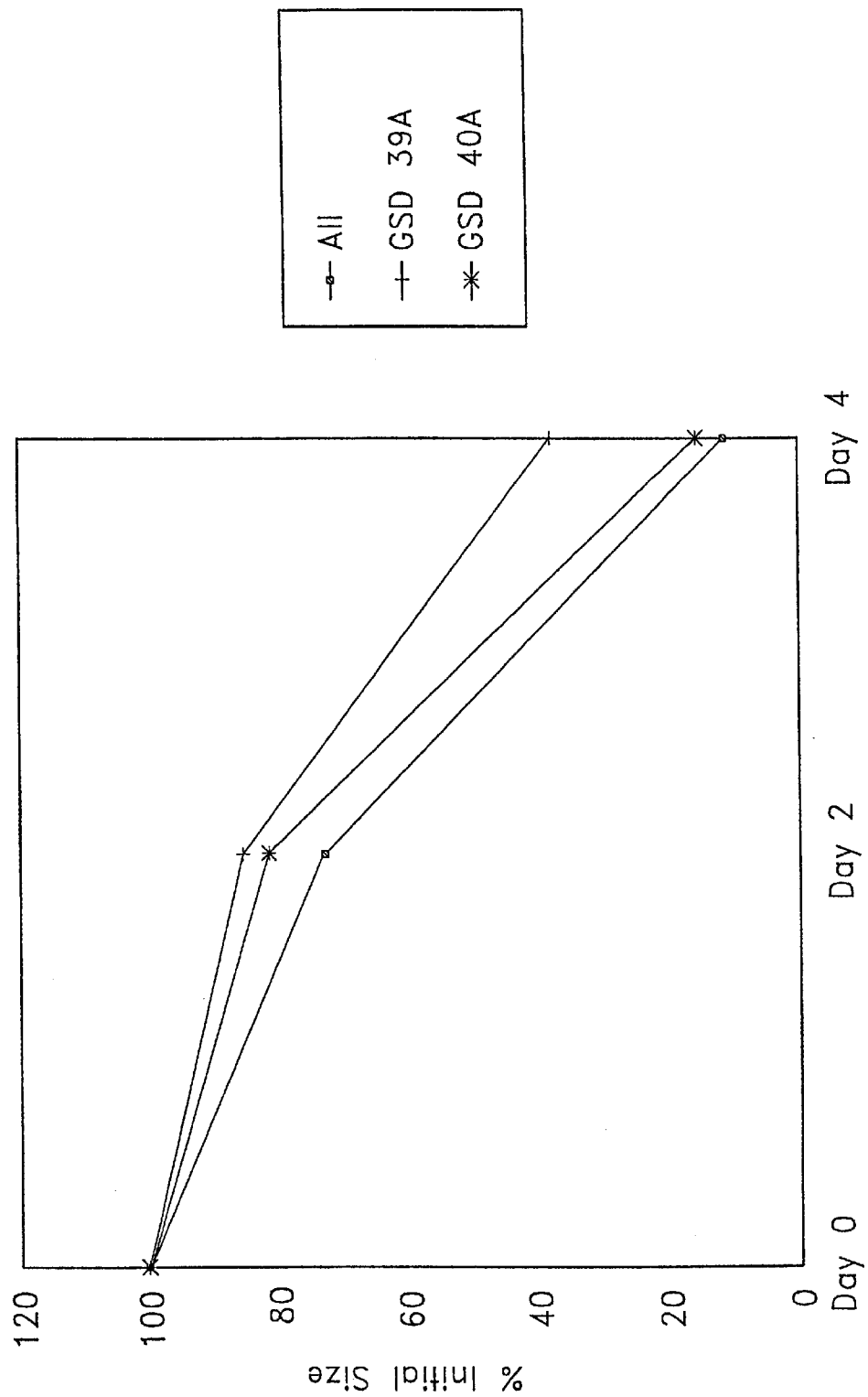
FIG. 11 illustrates the percentage change in size of granulation tissue for vehicle-treated wounds that served as controls for wounds treated either with AII, GSD-39A or GDS-40A shown in FIG. 12.
Figure 12:
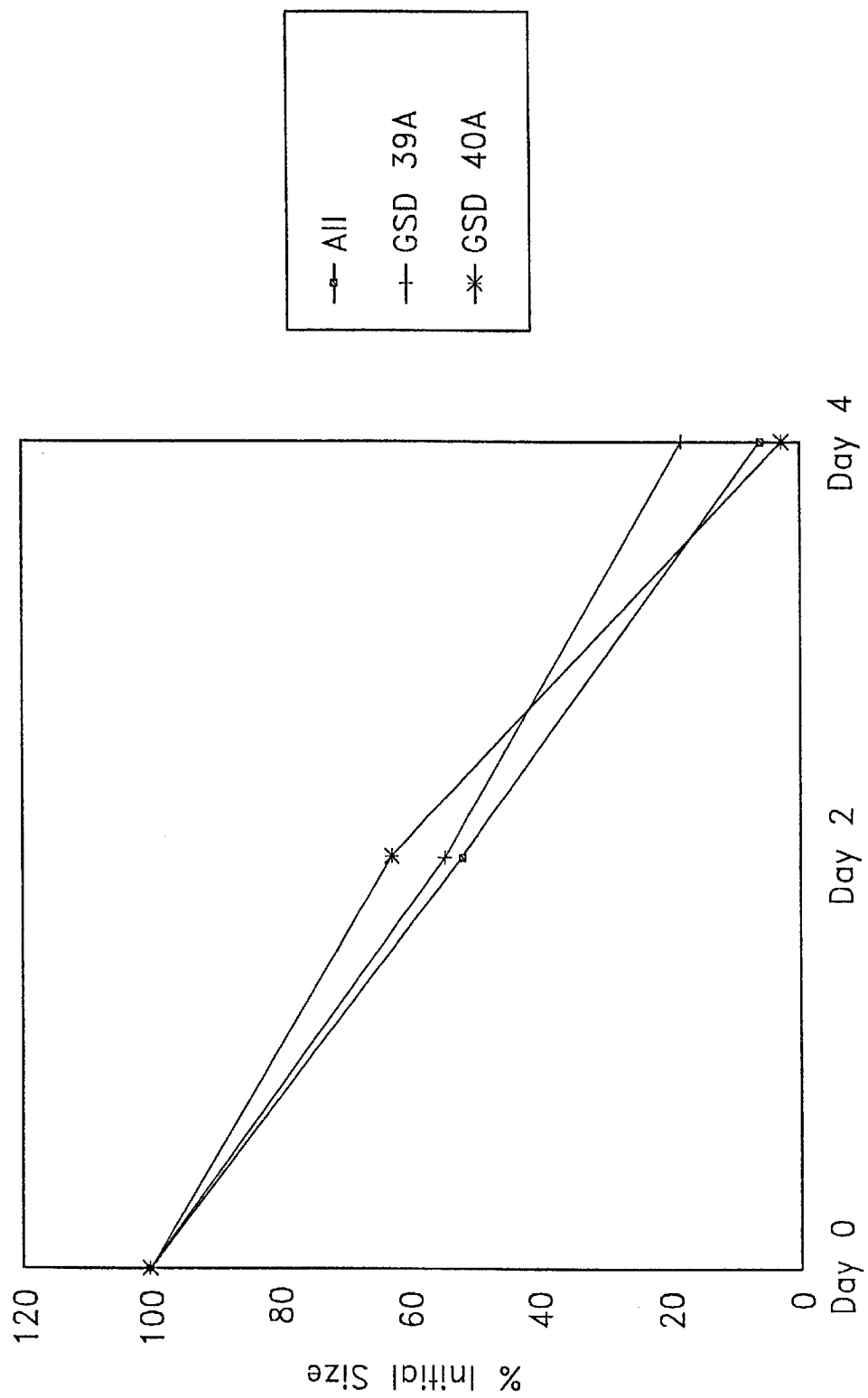
FIG. 12 illustrates the percentage change in size of granulation tissue for test wounds treated either with AII, GSD-39A or GDS-40A. Corresponding results from vehicle-treated controls are shown in FIG. 11.
Figure 13:
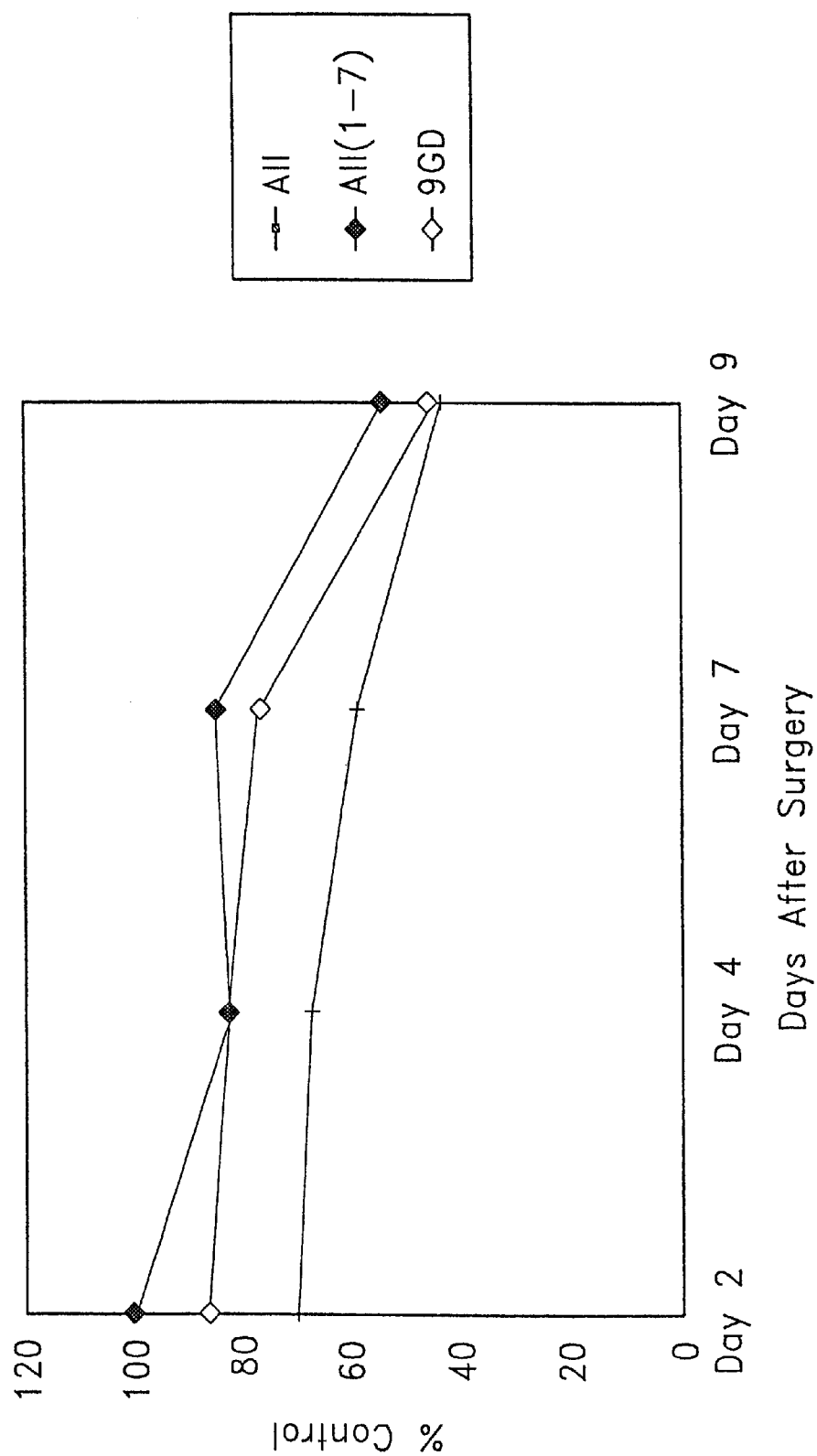
FIG. 13 illustrates the percent of control response in wound closure relative to vehicle-treated control using AII, AII(1–7) and norLeu$^3$ AII(1–7) (9GD).

As illustrated in FIGS. 1–6 and 13, wound closure was substantially accelerated relative to the control wounds when the test wounds were treated with Analogs 1–8 in accordance with the general formulae presented above. As illustrated in FIGS. 1–6 and 13, in every case, administration of one of the analogs accelerated the closure of the wound after surgery. FIGS. 7–12 illustrate the percent of control response in formation of granulation tissue. In every case, administration of one of the analogs accelerated the formation of granulation tissue compared to administration of vehicle alone. These results illustrate how AII analogs or analogs of AII fragments having amino acid sequences in accordance with the invention can be used to accelerate wound healing. Moreover, these results confirm that the invented compositions were characterized as unexpectedly strong promoters of healing for full thickness wounds.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and although specific terms have been employed herein, they are intended in a descriptive sense and not for purposes of limitation.

What is claimed is:

1. A peptide with an amino acid sequence consisting a sequence selected of the general formula:

R1-Arg-norLeu-R2-R3-His-Pro-R4, wherein R1 is selected from the group consisting of H and Asp;

R2 is selected from the group consisting of Tyr, Tyr(PO3)2, and homoSer;

R3 is selected from the group consisting of Ile and norLeu; and

R4 is selected from the group consisting of H, Phe, and Ile.

2. The peptide of claim 1 selected from the group consisting of SEQ ID NO:5, SEQ ID NO:9, and SEQ ID NO:15.

3. The peptide of claim 1 wherein R1 is Asp.

4. The peptide of claim 3 selected from the group consisting of SEQ ID NO:5 and SEQ ID NO:15.

5. The peptide of claim 3 wherein R5 is H.

6. The peptide of claim 5, wherein the peptide is SEQ ID NO:15.

7. A pharmaceutical composition comprising:

(a) an amount effective for accelerating wound healing of a peptide of claim 1; and (b) a pharmaceutically acceptable carrier.

8. A pharmaceutical composition comprising:

(a) an amount effective for accelerating wound healing of a peptide of claim 2; and (b) a pharmaceutically acceptable carrier.

9. A pharmaceutical composition comprising:

(a) an amount effective for accelerating wound healing of a peptide of claim 3; and (b) a pharmaceutically acceptable carrier.

10. A pharmaceutical composition comprising:

(a) an amount effective for accelerating wound healing of a peptide of claim 4; and (b) a pharmaceutically acceptable carrier.

11. A pharmaceutical composition comprising:
(a) an amount effective for accelerating wound healing of a peptide of claim 5; and
(b) a pharmaceutically acceptable carrier.

12. A pharmaceutical composition comprising:
(a) an amount effective for accelerating wound healing of a peptide of claim 6; and
(b) a pharmaceutically acceptable carrier.

13. A method for accelerating wound healing, comprising applying to a wound an amount effective to accelerate wound healing of a peptide according to claim 1.

14. The method of claim 13, wherein the method is used to treat a wound selected from the group consisting of burns, surgical incisions, lacerations, ulcers, and traumas.

* * * * *